(12) United States Patent
Grashow

(10) Patent No.: US 12,280,211 B2
(45) Date of Patent: Apr. 22, 2025

(54) NASAL PORTION AND PATIENT INTERFACE DEVICE INCLUDING SAME CROSS-REFERENCE TO RELATED APPLICATIONS

(71) Applicant: KONINKLIJKE PHILIPS N.V., Eindhoven (NL)

(72) Inventor: Jonathan Sayer Grashow, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 656 days.

(21) Appl. No.: 17/262,252

(22) PCT Filed: Aug. 16, 2019

(86) PCT No.: PCT/EP2019/071991
§ 371 (c)(1),
(2) Date: Jan. 22, 2021

(87) PCT Pub. No.: WO2020/038836
PCT Pub. Date: Feb. 27, 2020

(65) Prior Publication Data
US 2021/0260326 A1     Aug. 26, 2021

Related U.S. Application Data

(60) Provisional application No. 62/721,683, filed on Aug. 23, 2018.

(51) Int. Cl.
*A61M 16/06*     (2006.01)
(52) U.S. Cl.
CPC .... *A61M 16/0672* (2014.02); *A61M 16/0605* (2014.02); *A61M 16/0683* (2013.01); *A61M 2210/0618* (2013.01)

(58) Field of Classification Search
CPC .......... A61M 16/0672; A61M 16/0605; A61M 16/0683; A61M 16/00; A61M 16/0666;
(Continued)

(56) References Cited

U.S. PATENT DOCUMENTS 3,400,714 A  *  9/1968  Sheridan ........... A61M 16/0666
                                                128/207.18
5,477,852 A     12/1995  Disanza et al.
(Continued)

FOREIGN PATENT DOCUMENTS

WO    WO-2018203759 A1 * 11/2018 ............ A61M 16/06

OTHER PUBLICATIONS

International Search Report for PCT/EP2019/071991 dated Aug. 16, 2019.

*Primary Examiner* — Tu A Vo
*Assistant Examiner* — Kelsey E Baller
(74) *Attorney, Agent, or Firm* — Michael W. Haas

(57) ABSTRACT

A nasal portion is for a patient interface device of an airway pressure support system. The airway pressure support system includes a gas flow generator. The gas flow generator is configured to generate a flow of breathing gas to be delivered to an airway of a patient. The patient interface device is in fluid communication with the gas flow generator. The nasal portion includes an extension portion configured to be in fluid communication with the gas flow generator, and a cap member provided on the extension portion. The extension portion and the cap member each move between first and second positions, the cap member moving independently with respect to the extension portion when the extension portion and the cap member move between the first and second positions.

12 Claims, 9 Drawing Sheets

(58) Field of Classification Search
CPC .......... A61M 16/0667; A61M 16/0622; A61M 16/0616; A61M 2210/0618; A61M 15/08–085; A62B 23/06
See application file for complete search history.

(56) References Cited

U.S. PATENT DOCUMENTS

| | | | | |
|---|---|---|---|---|
| 5,533,506 A | * | 7/1996 | Wood ................ | A61M 16/0666 128/207.18 |
| 6,478,026 B1 | * | 11/2002 | Wood ................ | A61M 16/1055 128/207.18 |
| 9,032,955 B2 | | 5/2015 | Kwok et al. | |
| 2005/0011524 A1 | | 1/2005 | Chu et al. | |
| 2006/0124131 A1 | * | 6/2006 | Chandran ......... | A61M 16/0666 128/206.28 |
| 2007/0107737 A1 | * | 5/2007 | Landis .............. | A61M 16/0672 128/207.18 |
| 2009/0095303 A1 | * | 4/2009 | Sher ................. | A61M 16/0616 128/207.18 |
| 2009/0183739 A1 | | 7/2009 | Wondka | |
| 2009/0320851 A1 | | 12/2009 | Gale et al. | |
| 2010/0326441 A1 | * | 12/2010 | Zucker ............... | A61M 15/085 128/207.18 |
| 2012/0204870 A1 | | 8/2012 | Mcauley | |
| 2012/0318271 A1 | | 12/2012 | Ho | |
| 2015/0013685 A1 | * | 1/2015 | Haibach ............ | A61M 16/045 128/207.18 |
| 2015/0250973 A1 | * | 9/2015 | Allum ............... | A61M 16/201 128/205.25 |
| 2016/0074611 A1 | | 3/2016 | Dulabon et al. | |
| 2017/0007794 A1 | * | 1/2017 | Atherton ........... | A61M 16/125 |
| 2017/0119987 A1 | * | 5/2017 | Buddharaju ...... | A61M 16/0816 |
| 2017/0143926 A1 | | 5/2017 | Allum et al. | |
| 2019/0240438 A1 | * | 8/2019 | Stenzler ........... | A61M 16/0683 |

* cited by examiner

NASAL PORTION AND PATIENT INTERFACE DEVICE INCLUDING SAME CROSS-REFERENCE TO RELATED APPLICATIONS

CROSS-REFERENCE TO RELATED APPLICATIONS

This application claims the priority benefit under 35 U.S.C. § 371 of International Patent Application No. PCT/EP2019/071991, filed on Aug. 16, 2019, which claims the priority benefit of U.S. Provisional Application No. 62/721,683, filed on Aug. 23, 2018, the contents of which are herein incorporated by reference.

BACKGROUND OF THE INVENTION

1. Field of the Invention

The present invention pertains to nasal portions, and more particularly, to nasal portions for patient interface devices. The present invention also relates to patient interface devices including nasal portions.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. The mask component may also include pillows style nasal portions or nasal cannulas that are configured to extend into the interior of the patient's nostrils and engage therewith.

One known drawback with such mask components is that the pillows style nasal portions or nasal cannulas have a generally fixed opening through which the breathing gas exits. Because the pillows style nasal portions or nasal cannulas terminate in the interior of the patient's nostrils, these openings are generally relatively small. Such design imparts a restriction to the flow of breathing gas (more than the nostril would by itself) which can result in uncomfortable breathing sensations for the patient. Furthermore, existing cone-shaped pillows masks require that the pillows be compressed into the face in order to maintain a robust seal, which at times results in uncomfortable pressure points on the rather sensitive septum and nostrils. Additionally, the seal against the face of the patient is highly dependent on compressive forces exerted by the headgear, so movement or stretching of the headgear over time can significantly deteriorate the stability of the seal. Moreover, because the pillows style cushion, for example and without limitation, is resistant to deformation, the pillows style cushion often does not conform as easily to the shape of the patient's nostrils, resulting in pressure points and a reduced seal.

SUMMARY OF THE INVENTION

Accordingly, it is an object of the present invention to provide an improved nasal portion for a patient interface device, and a patient interface device including the same.

In accordance with one aspect of the disclosed concept, a nasal portion is provided for a patient interface device of an airway pressure support system. The airway pressure support system includes a gas flow generator. The gas flow generator is configured to generate a flow of breathing gas to be delivered to an airway of a patient. The patient interface device is in fluid communication with the gas flow generator. The nasal portion includes an extension portion configured to be in fluid communication with the gas flow generator, and a cap member provided on the extension portion. The extension portion and the cap member each move between first and second positions, the cap member moving independently with respect to the extension portion when the extension portion and the cap member move between the first and second positions.

In accordance with another aspect of the disclosed concept, a patient interface device is provided. The patient interface device includes a pair of the aforementioned nasal portions.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
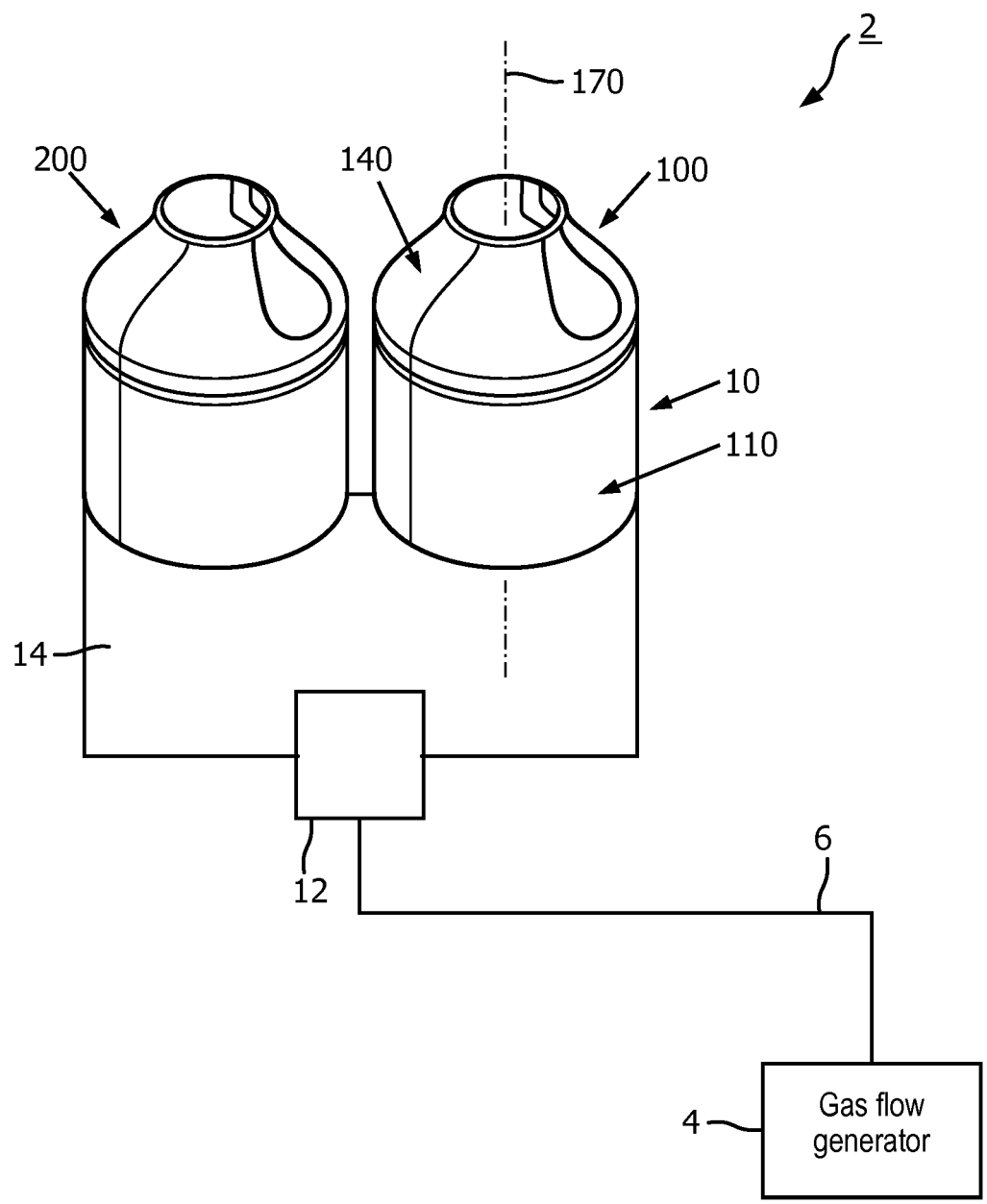
FIG. 1 is a partially simplified isometric view of an airway pressure support system and patient interface device for the same, in accordance with one non-limiting embodiment of the disclosed concept.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are joined or coupled together directly and are in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a partially simplified isometric view of an airway pressure support system 2, in accordance with one non-limiting embodiment of the disclosed concept. As shown, airway pressure support system 2 includes a gas flow generator 4 (shown in simplified form), a hose 6 (shown in simplified form) coupled to gas flow generator 4, and a novel patient interface device 10. Gas flow generator 4 is configured to generate a flow of breathing gas to be delivered to an airway of a patient. Patient interface device 10 is in fluid communication with hose 6 in order to receive the flow of breathing gas generated by gas flow generator 4.

In the example of FIG. 1, patient interface device 10 includes a coupling member (e.g., without limitation, elbow member 12) coupled to hose 6, a base portion 14, and a pair of nasal portions 100,200 each configured to extend into and sealingly engage against an interior of a corresponding nostril of a patient. It will be appreciated that base portion 14 is fluidly coupled to hose 6. As used herein, the phrase "fluidly coupled" or "fluidly connected" shall mean that a fluid pathway is provided between two or more components that are coupled together. Furthermore, elbow member 12 is coupled to base portion 14 and structured to be coupled to hose 6 in order to fluidly connect hose 6 to base portion 14.

In one example embodiment, nasal portions 100, 200 are each pillows style nasal portions. As employed herein, the term "pillows style" shall mean a generally cone-shaped sealing element, a top portion of the cone-shaped sealing element being designed to be small enough to be inserted into the nostril, and a wider bottom portion of the cone-shaped sealing element being designed to seal against an opening of the nostril. While nasal portion 200 is preferably configured and structured the same as nasal portion 100, for ease of illustration and economy of disclosure, only nasal portion 100 will be discussed and illustrated in detail herein.

Figure 2:
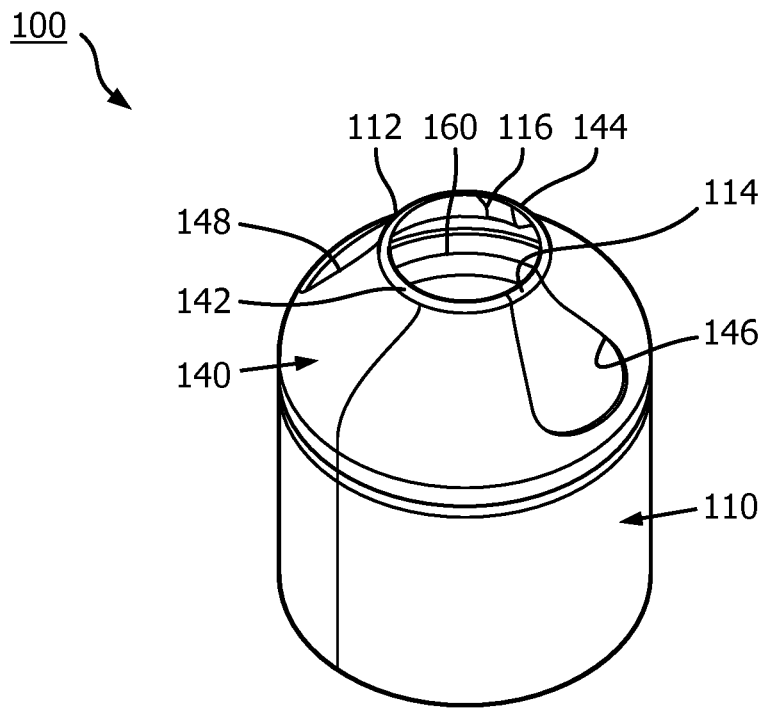
FIGS. 2 and 3 are isometric and exploded isometric views, respectively, of a nasal portion of the patient interface device of FIG. 1.
Figure 3:
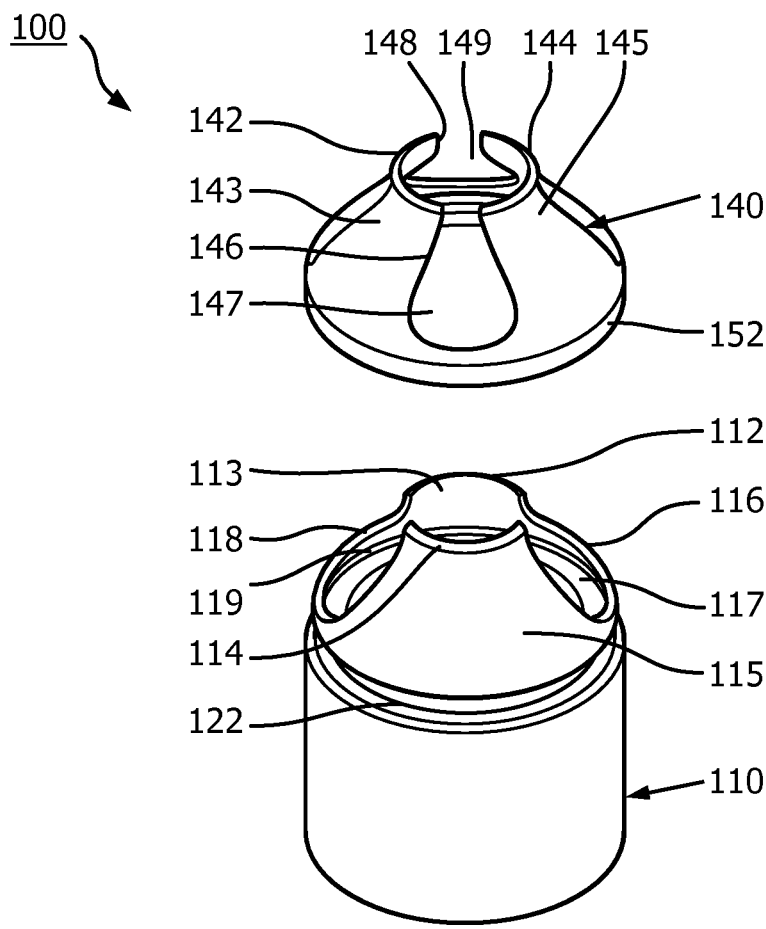
Figure 4:
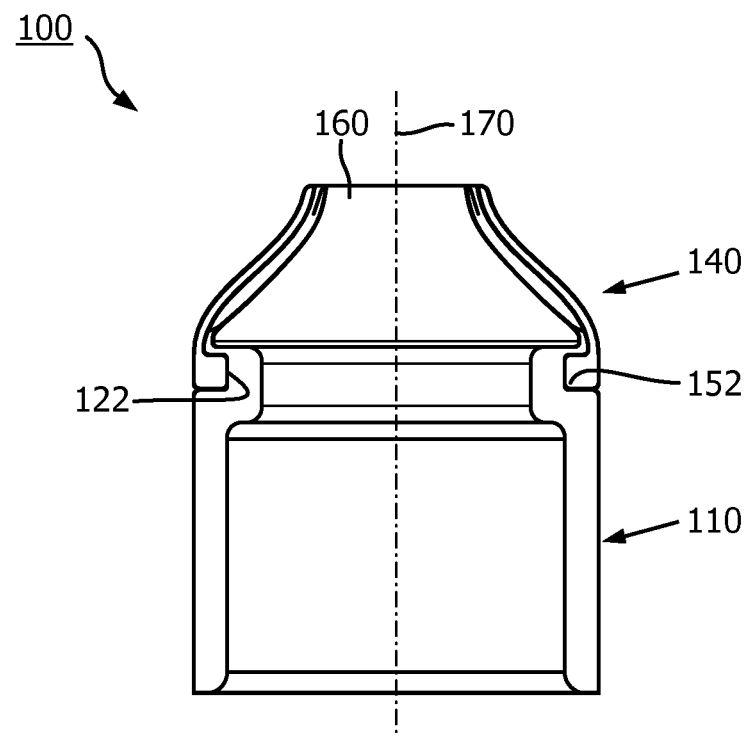
FIG. 4 is a section view of the nasal portion of FIG. 2.

FIGS. 2-4 show isometric, exploded isometric, and section views, respectively, of nasal portion 100. As shown most clearly in FIG. 3, nasal portion 100 includes an extension portion 110 and a cap member 140 provided on extension portion 110. In one example embodiment, extension portion 110 extends outwardly from and is in fluid communication with base portion 14. As used herein, the statement that two or more parts or components are in "fluid communication" with each other shall mean that a fluid pathway is provided between said parts or components. In this manner, breathing gas is able to be passed through base portion 14 and into extension portion 110. In an example embodiment, base portion 14 and extension portion 110 are a unitary component made from a single piece of material (e.g., without limitation, silicone), however, base portion 14 and extension portion 110 may also be formed separately without varying from the scope of the disclosed concept. Cap member 140 and extension portion 110 may be separate components coupled by a suitable coupling mechanism.

Figure 5:
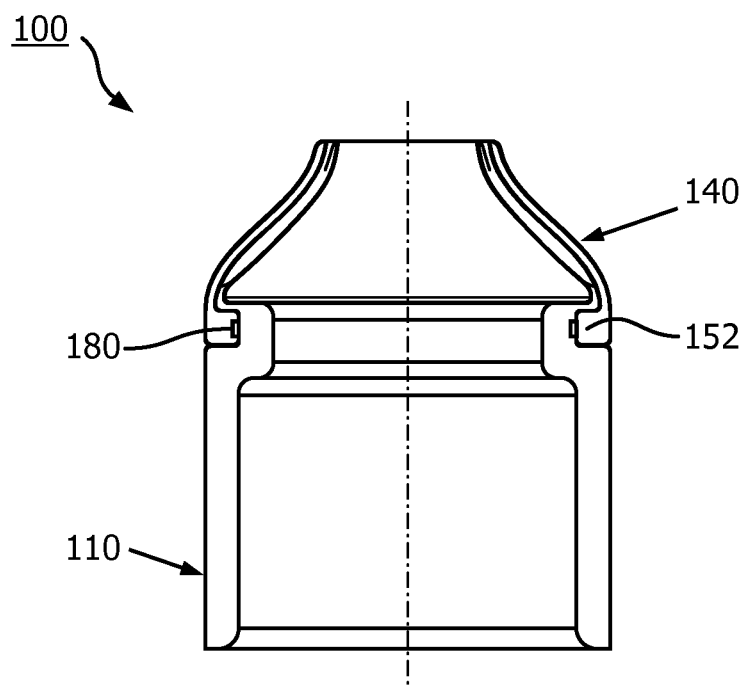
FIG. 5 is a section view of another nasal portion, in accordance with another non-limiting embodiment of the disclosed concept.

For example, as shown in FIG. 4, extension portion 110 and cap member 140 each have a corresponding annular-shaped coupling portion 122, 152. In one example embodiment the coupling portion of extension portion 110 is in the form of an annular-shaped grooved region 122, and the coupling portion of cap member 140 is in the form of an annular-shaped protrusion 152, protruding radially inwardly from an exterior of cap member 140 toward a common longitudinal axis 170 extending centrally through extension portion 110 and cap member 140. As shown, protrusion 152 is coupled to grooved region 122 via a snap-fit mechanism, and is located external with respect to extension portion 110. Alternatively, a suitable alternative nasal portion (e.g., nasal portion 100 shown in FIG. 5) may have a coupling portion 152 of a cap member 140 that is coupled to an extension portion 110 via an adhesive 180. While the aforementioned extension portions 110 and cap members 140 are manufactured as separate and distinct components, it will be appreciated that a similar suitable alternative nasal portion (not shown) may have an extension portion and cap member manufactured from a single piece of material (e.g., via co-molding).

Continuing to refer to FIG. 3, extension portion 110 and cap member 140 each have a number of distal edge portions 112, 114, 142, 144 and at least one intermediate edge portion 116, 118, 146, 148 connecting distal edge portions 112, 114, 142, 144 together. Extension portion 110 and cap member 140 each also have a number of flap portions 113, 115, 143, 145 and a number of cut-outs 117, 119, 147, 149. Cut-outs 117, 119, 147, 149 are voids that are bounded by corresponding intermediate edge portions 116, 118, 146, 148 and distal edge portions 112, 114, 142, 144. Distal edge portions 112, 114 are preferably coplanar, and when cap member 140 and extension portion 110 are assembled, distal edge portions 142, 144 of cap member 140 are preferably coplanar with distal edge portions 112, 114 of extension portion 110. Intermediate edge portions 116, 118 are preferably opposite and spaced from each other, and intermediate edge portions 146, 148 are also preferably opposite and spaced from each other. As shown in FIG. 2, distal edge portions 112, 114 of extension portion 110 and distal edge portions 142, 144 of cap member 140 together define an opening 160 through which the flow of breathing gas exits nasal portion 100 and passes through the airway of the patient. In the exemplary embodiment, intermediate edge portions 116, 118 of extension portion 110 are located substantially internal with respect to cap member 140. As such, cap member 140 is located external with respect to extension portion 110 and is configured to be sealingly engaged with intermediate edge portions 116, 118. Furthermore, intermediate edge portions 146, 148 of cap member 140 are substantially located external with respect to extension portion 110.

Figure 6:
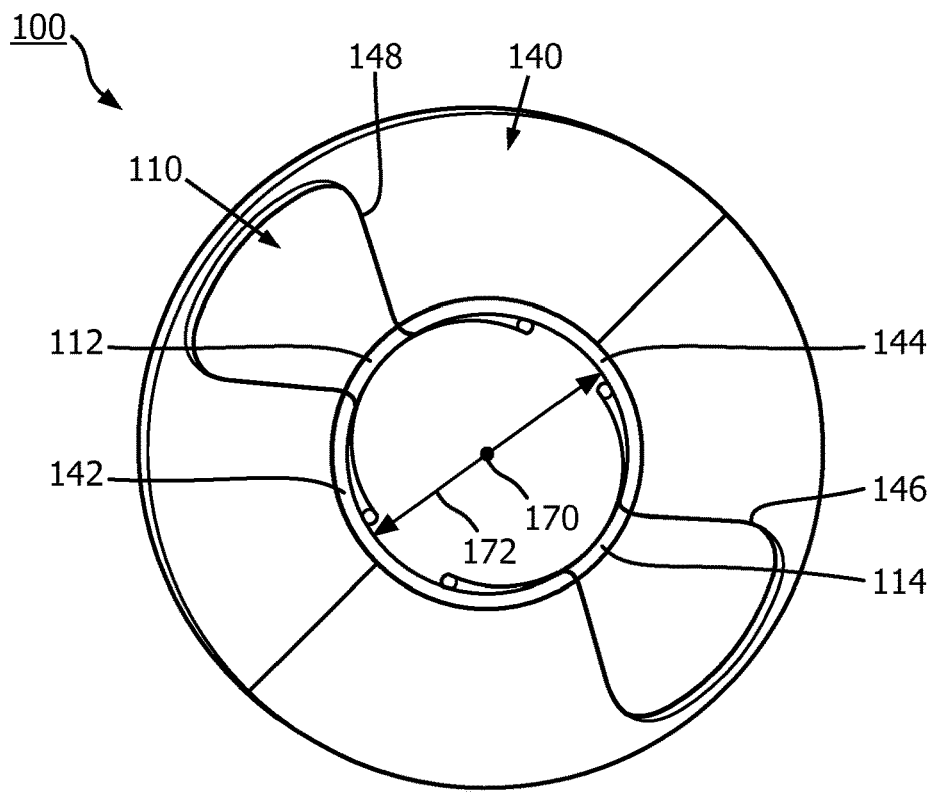
FIG. 6 is a top view of the nasal portion of FIG. 2, shown with the extension portion and the cap member disposed in a first position.
Figure 7:
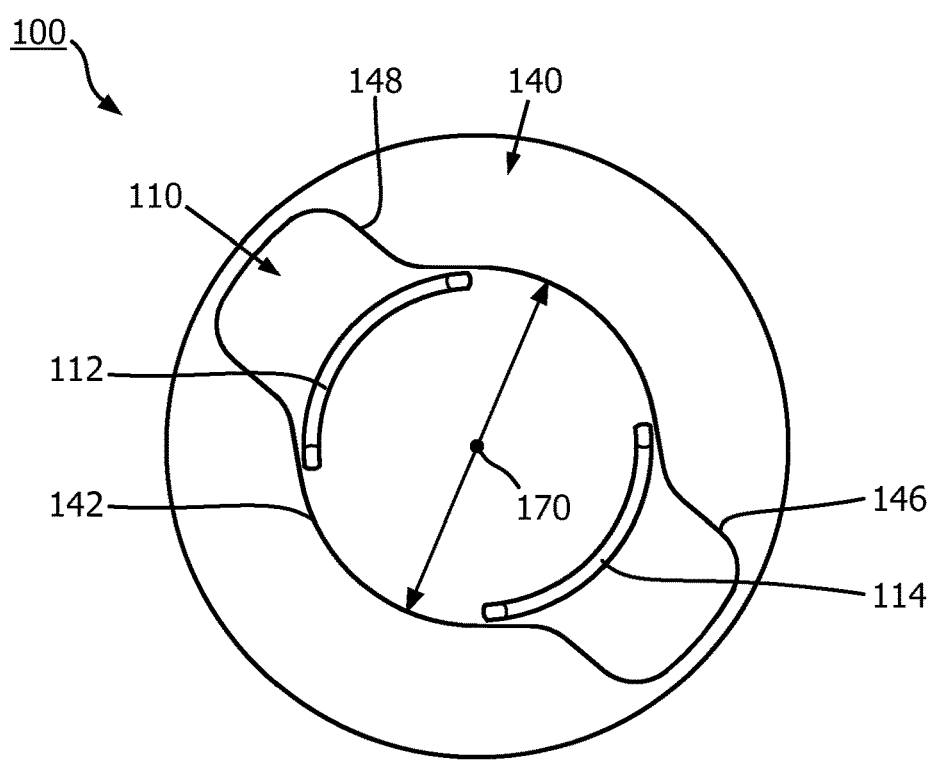
FIG. 7 is another top view of the nasal portion of FIG. 2, shown with the extension portion and the cap member disposed in a second position.

Unlike known nasal portions (not shown), nasal portion 100 is configured to move between positions to provide a number of advantages. More specifically, and referring to FIGS. 6 and 7, extension portion 110 and cap member 140 are each structured to move between a first position (FIG. 6) and a second position (FIG. 7), cap member 140 moving independently with respect to extension portion 110 when extension portion 110 and cap member 140 move between the first and second positions. As FIGS. 6 and 7 are top views of nasal portion 100, it will be appreciated that longitudinal axis 170 (represented by a dot) extends into and out of the page, and is perpendicular to the plane of the page. In comparing FIGS. 6 and 7, it can be seen that when cap member 140 and extension portion 110 move from the first position to the second position, cap member 140 and extension portion 110 each expand radially outwardly with respect to longitudinal axis 170. For example, in the first position of FIG. 6, the opening has a first diameter 172, and in the second position of FIG. 7, the opening has a second diameter 174 larger than the first diameter 172. In any event, while the opening may not always be circular, it can be appreciated that the area of the opening increases from the first position to the second position.

In order to achieve this movement, when, for example, breathing gas is passed through nasal portion 100, distal edge portions 112, 114, 142, 144 slide with respect to each other. That is, it can be appreciated (see FIGS. 6 and 7) that when moving from the first position to the second position, distal edge portions 112, 114 of extension portion 110 are pressed into the spaces between distal edge portions 142, 144 by the breathing gas, thus causing the size of the exit opening 160 to expand. When patient interface device 10 (FIG. 1) is donned by the patient, and a flow of breathing/treatment gas is provided, opening 160 is enlarged as the breathing gas exits through nasal portion 100 and into the patient's airway. Moreover, because the size of the primary exit opening is enlarged, the pressure drop associated with the breathing gas existing nasal portion 110 likewise decreases, thus resulting in a more pleasant delivery of pressure support therapy to the patient. Accordingly, the patient is provided with a more comfortable experience using patient interface device 10. Furthermore, this results in a sealing element which is less dependent on precise headgear forces to maintain sealing performance over time.

Figure 8:
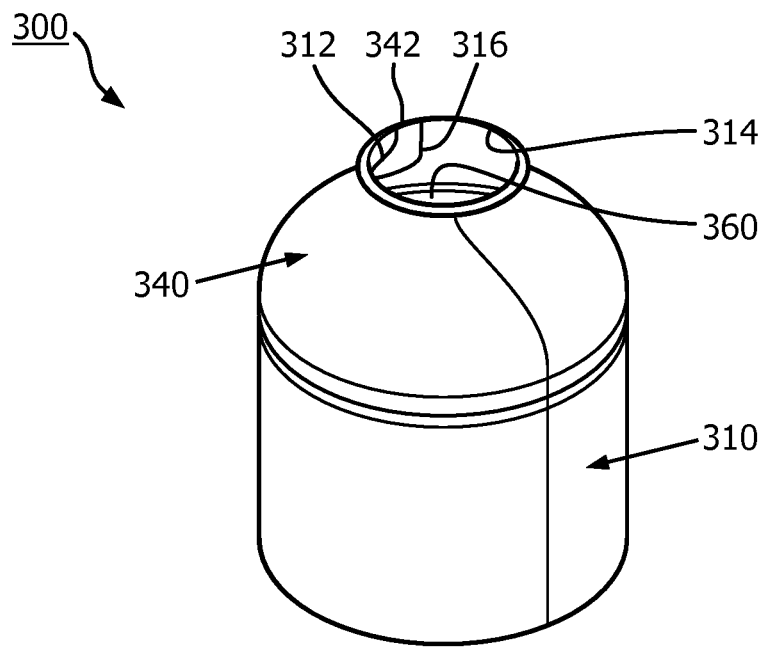
FIGS. 8 and 9 are isometric and exploded isometric views, respectively, of another nasal portion, in accordance with another non-limiting embodiment of the disclosed concept.
Figure 9:
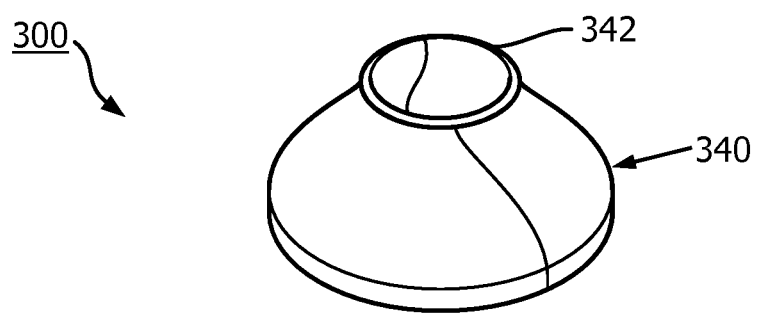
Figure 9:
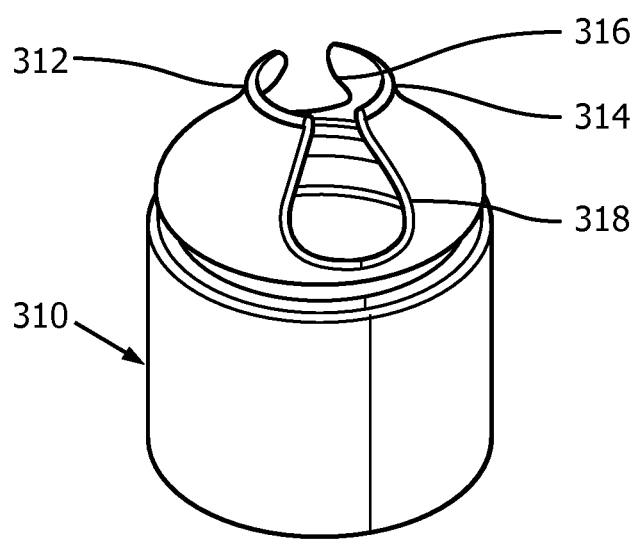

FIGS. 8 and 9 are isometric and exploded isometric views, respectively, of another nasal portion 300, that may be implemented in patient interface device 10 in place of either of nasal portions 100, 200, in accordance with another non-limiting example embodiment of the disclosed concept. Nasal portion 300 is structured similar to nasal portions 100, 200, discussed above, and like numbers designate like components. As shown more clearly in FIG. 9, extension portion 310 is structured substantially the same as extension portion 110. That is, extension portion 310 has opposing distal edge portions 312, 314, and intermediate edge portions 316, 318 extending between the distal edge portions 312, 314. However, unlike nasal portion 100, nasal portion 300 is provided with a cap member 340 having only one single distal edge portion 342. As shown in FIG. 8, when assembled on extension portion 310, distal edge portion 342 of cap member 340 is generally coplanar with and located external with respect to distal edge portions 312, 314. It will, however, be appreciated that a suitable alternative nasal portion need not have coplanar distal edge portions, without departing from the scope of the disclosed concept. Additionally, unlike cap member 140, cap member 340 is structured and configured to be relatively thin (e.g., without limitation, 0.05-0.5 millimeters), thereby allowing for movement between first and second positions in a similar manner as discussed above with respect to nasal portion 100. Specifically, when moving between first and second positions, internal air pressures cause distal edge portions 312, 314 to expand radially outwardly, and also cause the single distal edge portion 342 of cap member 340 to expand radially outwardly. Thus, it can be appreciated that a primary exit opening 360 of nasal portion 300 is enlarged in substantially the same manner in which opening 160 of nasal portion 100, discussed above, is enlarged.

Furthermore, by substantially surrounding intermediate edge portions 316, 318, it will be appreciated that cap member 340 performs the additional function of minimizing the number of leak points between extension portion 310 and cap member 340. For example, breathing gas passing proximate intermediate edge portions 316, 318 which may enter into the space between the exterior of extension portion 310 and the interior of cap member 340, will advantageously not have a location to exit nasal portion 300 other than proximate the primary exit opening.

Figure 10:
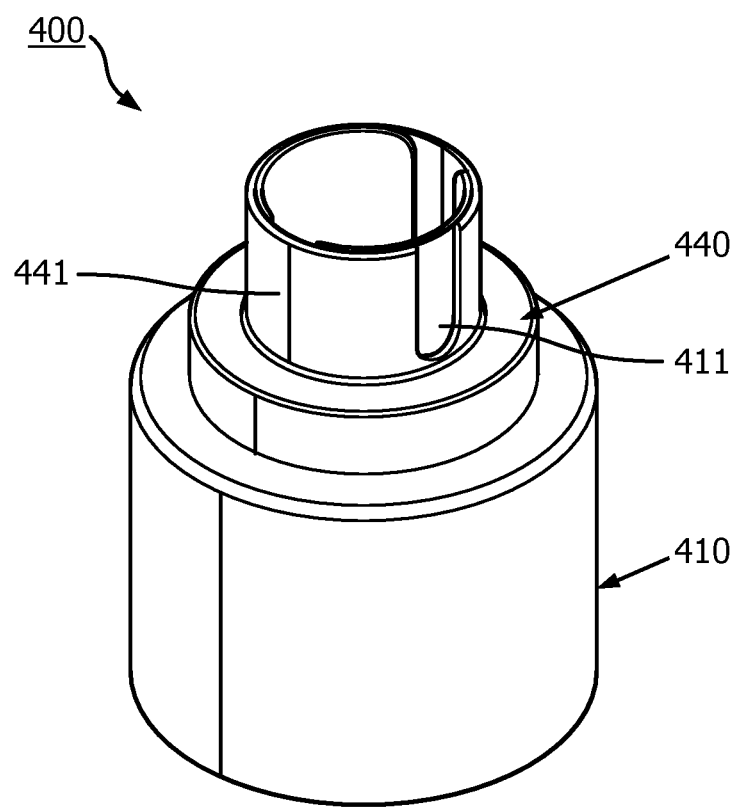
FIGS. 10 and 11 are isometric and exploded isometric views, respectively, of another nasal portion, in accordance with another non-limiting embodiment of the disclosed concept.
Figure 11:
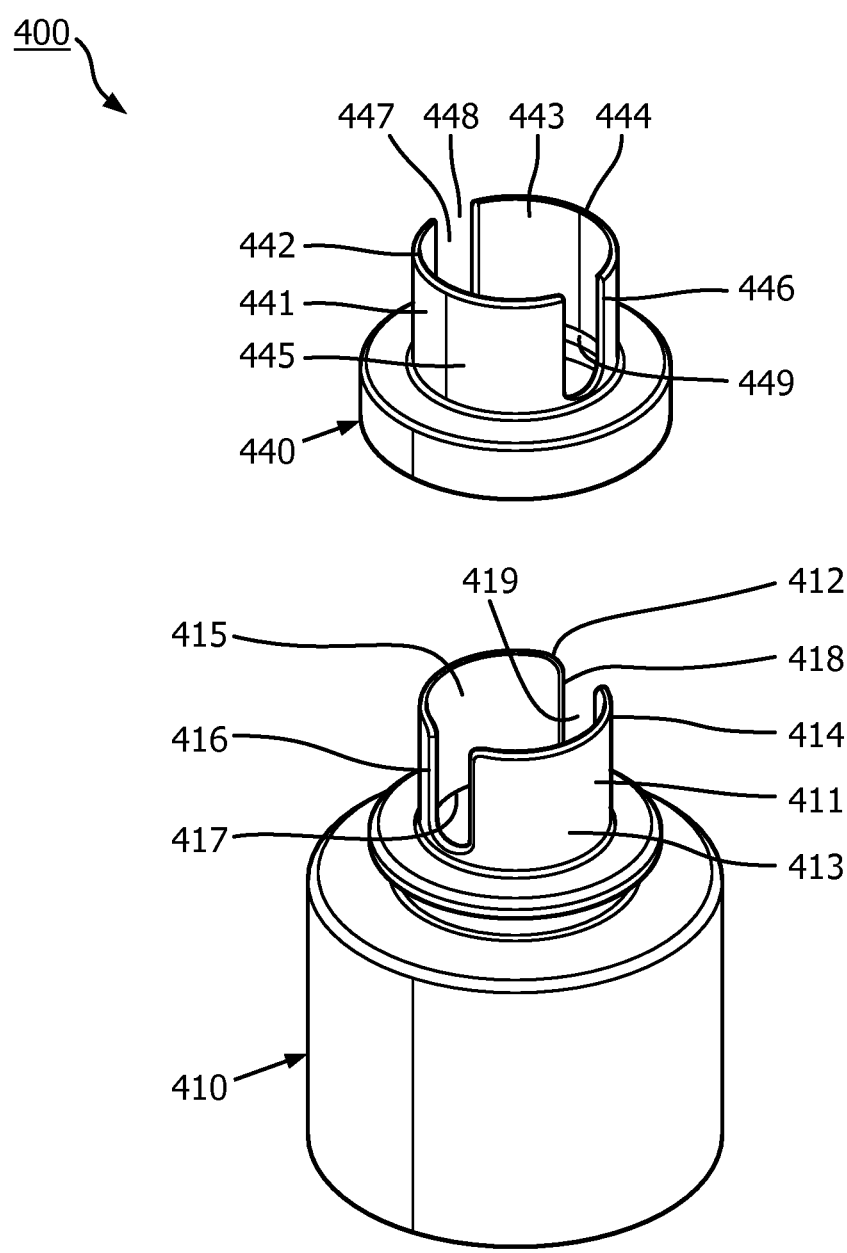

FIGS. 10 and 11 are isometric and exploded isometric views, respectively, of another nasal portion 400, in accordance with another non-limiting embodiment of the disclosed concept. Nasal portion 400 is structured similar to nasal portions 100, 200, 300, discussed above, and like numbers designate like components, however, nasal portion 400 is a nasal cannula. As employed herein, the phrase "nasal cannula" shall mean a generally cylindrical-shaped element designed to be inserted into a nostril and seal against interior surfaces of the nostril. For example, as shown in FIG. 11, extension portion 410 has a generally cylindrical-shaped portion 411 extending from distal edge portions 412, 414 and intermediate edge portions 416, 418. Similarly cap member 440 has a generally cylindrical-shaped portion 441 extending from distal edge portions 442, 444 and intermediate edge portions 446, 448. Extension portion 410 and cap member 440 each also have a number of flap portions 413, 415, 443, 445 and a number of cut-outs 417, 419, 447, 449. Cut-outs 417, 419, 447, 449 are voids that are bounded by corresponding intermediate edge portions 416, 418, 446, 448 and distal edge portions 412,414,442,444. Accordingly, it will be appreciated that in addition to pillows style nasal portions 100, 200, 300, a nasal portion 400 being a nasal cannula is contemplated herein. Specifically, nasal portion 400 is configured to flare outwardly from a first position to a second position to engage the nostril and provide a larger flow path.

Figure 12:
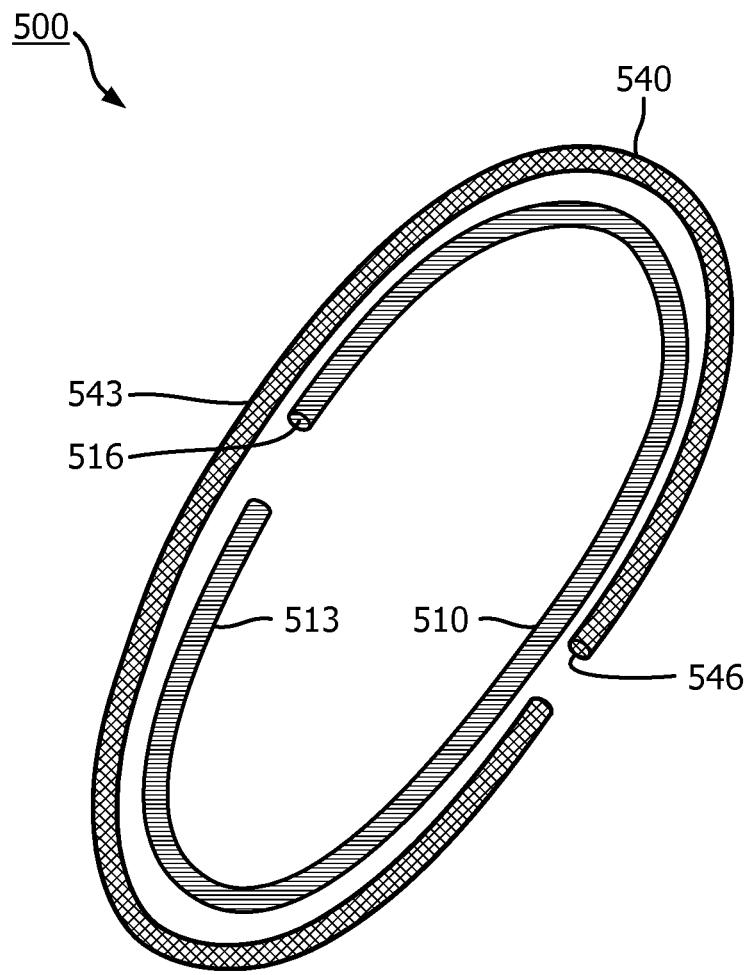
FIG. 12 is a section view of another nasal portion, in accordance with another non-limiting embodiment of the disclosed concept.
Figure 13:
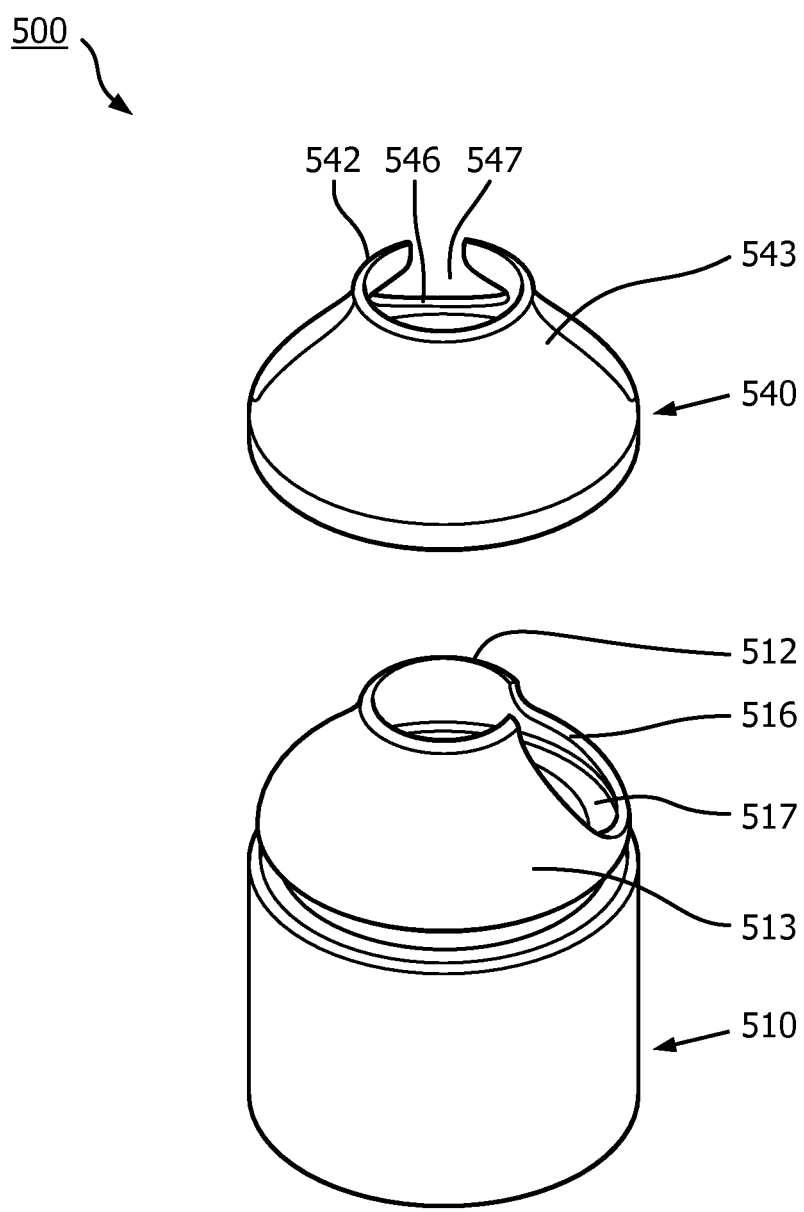
FIG. 13 is an exploded isometric view of the nasal portion of FIG. 12.

FIGS. 12 and 13 are section and exploded isometric views, respectively, of another nasal portion 500 that may be implemented into patient interface device 10 (FIG. 1) in place of either of nasal portions 100, 200, in accordance with another non-limiting embodiment of the disclosed concept. Nasal portion 500 is structured similar to nasal portions 100, 200, 300, 400, discussed above, and like numbers designate like components. However, as shown, both extension portion 510 and cap member 540 each only have one single corresponding intermediate edge portion 516, 546. For example, as shown in FIG. 13, extension portion 510 and cap member 540 each have one single flap portion 513, 543 and one single cut-out 517, 547. Cut-outs 517, 547 are voids that are bounded by intermediate edge portions 516, 546 and distal edge portions 512, 542. Accordingly, it will be appreciated that nasal portion 500 has a mechanism to minimize the number of potential locations for breathing gas to exit besides the primary exit opening. Specifically, upon entering extension portion 510 and passing toward the interior of the patient's nostril, rather than having two potential side exit openings (e.g., via two opposing intermediate edge portions), extension portion 510 only has one single intermediate edge portion 516 that could provide a potential pathway for breathing gas to escape. Furthermore, even if such breathing gas escaped through intermediate edge portion 516 to the space between the exterior of extension portion 510 and the interior of cap member 540, cap member 540 is only provided with one single intermediate edge portion 546 through which said breathing gas could escape.

Accordingly, it will be appreciated that the disclosed concept provides for an improved (e.g., reduced pressure drop upon exiting the nasal portion, more comfortable, less need for precise headgear forces) nasal portion 100, 200, 300, 400, 500 and patient interface device 10 including the same.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A nasal portion for a patient interface device of an airway pressure support system, the airway pressure support system comprising a gas flow generator, the gas flow generator being configured to generate a flow of breathing gas to be delivered to an airway of a patient, the patient interface device being in fluid communication with the gas flow generator in order to receive the flow of breathing gas generated by the gas flow generator, the nasal portion comprising:

an extension portion comprising a base configured to be in fluid communication with the gas flow generator, a conical end portion coupled to the base, and a first annular-shaped coupling portion disposed between the conical end portion and the base, wherein the conical end portion includes an exit opening defined in a distal end of the conical end portion, a first side opening defined on a first side of the conical end portion, and a second side opening defined on a second side of the conical end portion opposite the first side of the conical end portion, wherein the first side opening and the second side opening in the conical end portion are generally aligned along a first axis; and a conical shaped cap member defining an exit opening and being provided on the extension portion such that conical end portion of the extension portion extends into an interior of the cap member and such that the exit opening is coaxially aligned with the exit opening of the extension portion, wherein the cap member includes a second annular-shaped coupling portion adapted to engage the first annular-shaped coupling portion, wherein the cap member includes a first side opening defined on a first side of the cap member and a second side opening defined on a second side of the cap member opposite the first side of the cap member, wherein the first side opening and the second side opening of the cap member are generally aligned along a second axis, wherein the first axis and the second axis are perpendicular to one another.

2. The nasal portion according to claim 1, wherein a shape of the conical end portion of the extension portion and a shape of the cap member are similar.

3. The nasal portion according to claim 1, wherein the first annular-shaped coupling portion is coupled to the second annular-shaped coupling portion via an adhesive.

4. The nasal portion according to claim 1, wherein the first annular-shaped coupling portion is coupled to the second annular-shaped coupling portion via a snap-fit mechanism.

5. The nasal portion according to claim 1, wherein the exit opening in the conical end portion, the first side opening in the extension portion, and the second side opening in the extension portion are combined forming a continuous opening.

6. The nasal portion according to claim 1, wherein the exit opening in the cap member, the first side opening in the cap member, and the second side opening in the cap member are combined forming a continuous opening.

7. A patient interface device of an airway pressure support system, the airway pressure support system comprising a gas flow generator, the gas flow generator being configured to generate a flow of breathing gas to be delivered to an airway of a patient, the patient interface device comprising:

a pair of nasal portions each configured to extend into and sealingly engage against an interior of a corresponding nostril of the patient, each nasal portion comprising:

an extension portion comprising a base configured to be in fluid communication with the gas flow generator, a conical end portion coupled to the base, and a first annular-shaped coupling portion disposed between the conical end portion and the base, wherein the conical end portion includes an exit opening defined in a distal end of the conical end portion, a first side opening defined on a first side of the conical end portion, and a second side opening defined on a second side of the conical end portion opposite the first side of the conical end portion, wherein the first side opening and the second side opening in the conical end portion are generally aligned along a first axis; and a conical shaped cap member defining an exit opening and being provided on the extension portion such that conical end portion of the extension portion extends into an interior of the cap member and such that the exit opening is coaxially aligned with the exit opening of the extension portion, wherein the cap member includes a second annular-shaped coupling portion adapted to engage the first annular-shaped coupling portion, wherein the cap member includes a first side opening defined on a first side of the cap member and a second side opening defined on a second side of the cap member opposite the first side of the cap member, wherein the first side opening and the second side opening of the cap member are generally aligned along a second axis, wherein the first axis and the second axis are perpendicular to one another.

8. The nasal portion according to claim 7, wherein a shape of the conical end portion of the extension portion and a shape of the cap member are similar.

9. The patient interface according to claim 7, wherein the first annular-shaped coupling portion is coupled to the second annular-shaped coupling portion via an adhesive.

10. The patient interface according to claim 7, wherein the first annular-shaped coupling portion is coupled to the second annular-shaped coupling portion via a snap-fit mechanism.

11. The patient interface according to claim 7, wherein the exit opening in the conical end portion, the first side opening in the extension portion, and the second side opening in the extension portion are combined forming a continuous opening.

12. The patient interface according to claim 7, wherein the exit opening in the cap member, the first side opening in the cap member, and the second side opening in the cap member are combined forming a continuous opening.

* * * * *